US006435037B1

(12) United States Patent
Doten

(10) Patent No.: US 6,435,037 B1
(45) Date of Patent: Aug. 20, 2002

(54) MULTIPLEXED PHASE DETECTOR

(75) Inventor: Gregory P. Doten, Crystal, MN (US)

(73) Assignee: Data Sciences International, Inc., St. Paul, MN (US)

(*) Notice: Subject to any disclaimer, the term of this patent is extended or adjusted under 35 U.S.C. 154(b) by 0 days.

(21) Appl. No.: 09/479,268

(22) Filed: Jan. 6, 2000

(51) Int. Cl.[7] ................................................ G01F 1/66
(52) U.S. Cl. .................................. 73/861.27; 73/861.29
(58) Field of Search ........................ 73/861.25, 861.26, 73/861.27, 861.28, 861.29; 702/370; 331/17, 25, 27; 327/3, 156; 375/360, 328

(56) References Cited

U.S. PATENT DOCUMENTS

| 3,575,050 A | * | 4/1971 | Lynnworth | ................ 73/861.28 |
| 4,001,603 A |   | 1/1977 | Wilcox | ........................ 303/232 |
| 4,001,680 A |   | 1/1977 | Bylund et al. | ................. 324/78 |

(List continued on next page.)

FOREIGN PATENT DOCUMENTS

| CA | 1153795   | 9/1983  | ............. H03L/7/08 |
| DE | 19617635  | 11/1997 | ............. H03L/7/08 |
| EP | 0252444   | 7/1987  | ............. H03L/7/00 |
| EP | 0402711   | 12/1990 | ........... H03L/7/089 |
| EP | 0588599   | 3/1994  | ............. G01F/1/66 |
| EP | 0711041   | 11/1994 | ............. H03L/7/14 |
| EP | 0803984   | 3/1997  | ........... H03L/7/093 |

OTHER PUBLICATIONS

Drost, C.J., "Vessel Diameter–Independent Volume Flow Measurements Using Ultrasound", *Proceedings of the San Diego Biomedical Symposium* (J. Martin et al., Eds.), vol. 17, 299–302, (1978).

Hartley, C.J., "A Phase Detecting Ultrasonic Flowmeter", *25th ACEMB—Americana Hotel*, Bal Harbour, Florida, Oct. 1–5, 1972, Supported by NIH Grant HE–03251–08., 7 pgs.,.

Nagata, M., "A PWM Signal Processing Core Circuit Based on a Switched Current Integration Technique", *IEEE Journal of Solid–State Circuits*, vol. 33, No. 1, pp. 53–60, (Jan. 1998).

"Transonic Extracorporeal Products", http://www.transonic.com/body_extracorporeal.html, Transonic Systems Inc., Ithaca, NY, 7 p., (1996).

"Manual for System 5 SVT2 Module, Triton Technology, Inc.", 1–18, (Jun. 16, 1997).

Johansson, H.O., "A Simple Precharged CMOS Phase Frequency Detector", *IEEE Journal of Solid–State Circuits*, 33(2), pp. 295–299, (Feb. 1998).

Maeda, T., et al., "An Ultra–Low–Power–Consumption High–Speed GaAs Quasi–Differential Switch Flip–Flop (QD–FF)", *IEEE Journal of Solid–State Circuits*, 31(9), pp. 1361–1363, (Sep. 1996).

Rothermel, A., et al., "Analog Phase Measuring Circuit for Digital CMOS IC's", *IEEE Journal of Solid–State Circuits*, 28 (7), pp. 853–856, (Jul. 1993).

Somasekhar, D., et al., "Differential Current Switch Logic: A Low Power DCVS Logic Family", *IEEE Journal of Solid–State Circuits*, 31(7), pp. 981–991, (Jul. 1996).

Soyuer, M., et al., "High–Frequency Phase–Locked Loops in Monolithic Bipolar Technology", *IEEE Journal of Solid–State Circuits*, 24 (3), pp. 787–795, (Jun. 1989).

*Primary Examiner*—Harshad Patel
(74) *Attorney, Agent, or Firm*—Schwegman, Lundberg, Woessner & Kluth, P.A.

(57) ABSTRACT

A method for detecting a phase difference is provided. The method includes selecting first and second input signals from a plurality of pairs of input signals. The method further includes modulating a duty cycle of first and second intermediate signals from a first duty cycle based on a phase difference between the first and second input signals. The method also includes creating a differential signal based on the modulated duty cycles of the first and second intermediate signals that is related to the phase difference between the first and second input signals.

29 Claims, 10 Drawing Sheets

U.S. PATENT DOCUMENTS

| | | | |
|---|---|---|---|
| 4,011,503 A | 3/1977 | Ferrara | 324/83 |
| 4,015,470 A | 4/1977 | Morrison | 73/194 A |
| 4,022,058 A | 5/1977 | Brown | 73/194 |
| 4,055,814 A | 10/1977 | Abraham et al. | |
| 4,068,184 A | 1/1978 | Ahmed | 330/257 |
| 4,109,523 A | 8/1978 | Teyssandier | 73/194 A |
| 4,185,498 A | 1/1980 | Watson et al. | |
| 4,194,166 A | 3/1980 | Sakai et al. | 330/257 |
| 4,227,407 A | 10/1980 | Drost | 73/194 |
| 4,265,126 A | 5/1981 | Papadofrangakis et al. | 73/861 |
| 4,308,754 A | 1/1982 | Pedersen et al. | 73/861.28 |
| 4,312,238 A | 1/1982 | Rey | 73/861.28 |
| 4,316,150 A | 2/1982 | Crosby | 331/1 A |
| 4,365,204 A | 12/1982 | Haque | 328/127 |
| 4,383,202 A | 5/1983 | Beck et al. | 315/200 A |
| 4,384,491 A | 5/1983 | Brown et al. | 73/861.28 |
| 4,520,319 A | 5/1985 | Baker | 328/133 |
| 4,524,333 A | 6/1985 | Iwata et al. | 331/17 |
| 4,557,148 A | 12/1985 | Akiyama | 73/861.28 |
| 4,585,989 A | 4/1986 | Matney | 324/83 |
| 4,629,914 A | 12/1986 | Okanobu | 307/510 |
| 4,633,719 A | 1/1987 | Vander Heyden | 73/861.28 |
| 4,808,856 A | 2/1989 | Tanigawa | 307/511 |
| 4,870,303 A | 9/1989 | McGinn | 328/155 |
| 4,922,750 A | * 5/1990 | Magori | 73/861.29 |
| 4,947,852 A | 8/1990 | Nassi et al. | 128/662.06 |
| 5,035,147 A | 7/1991 | Woodward | 73/861.28 |
| 5,078,148 A | 1/1992 | Nassi et al. | 128/661.09 |
| 5,103,123 A | 4/1992 | McGinn | 307/514 |
| 5,117,698 A | 6/1992 | Baumoel | 73/861.28 |
| 5,121,639 A | 6/1992 | McShane | |
| 5,121,749 A | 6/1992 | Nassi et al. | 128/692 |
| 5,142,555 A | 8/1992 | Whiteside | 375/81 |
| 5,200,980 A | 4/1993 | Briddell | 375/83 |
| 5,339,816 A | 8/1994 | Akamatsu et al. | 128/661.09 |
| 5,440,936 A | 8/1995 | Spani et al. | 73/861.28 |
| 5,461,921 A | * 10/1995 | Papadakis et al. | 73/628 |
| 5,515,721 A | 5/1996 | Kim et al. | 73/170.13 |
| 5,553,505 A | 9/1996 | Bignell et al. | 73/861.28 |
| 5,577,079 A | 11/1996 | Zenno et al. | 375/373 |
| 5,585,756 A | 12/1996 | Wang | 327/341 |
| 5,659,268 A | 8/1997 | Kesner | 331/1 A |
| 5,663,666 A | 9/1997 | Chu et al. | 327/7 |
| 5,669,685 A | 9/1997 | Kotani et al. | 353/28 |
| 5,694,062 A | 12/1997 | Welch et al. | 327/3 |
| 5,695,092 A | * 12/1997 | Schrandt | 222/1 |
| 5,747,689 A | * 5/1998 | Hampo et al. | 73/304 C |
| 5,757,868 A | 5/1998 | Kelton et al. | 375/360 |
| 5,767,736 A | 6/1998 | Lakshmikumar et al. | 327/536 |
| 5,774,084 A | 6/1998 | Brombaugh et al. | 341/152 |
| 5,785,657 A | 7/1998 | Breyer et al. | 600/454 |
| 5,865,749 A | 2/1999 | Doten et al. | |
| 5,953,386 A | 9/1999 | Anderson | 375/376 |
| 5,970,106 A | 10/1999 | Izumikawa | 375/376 |

* cited by examiner

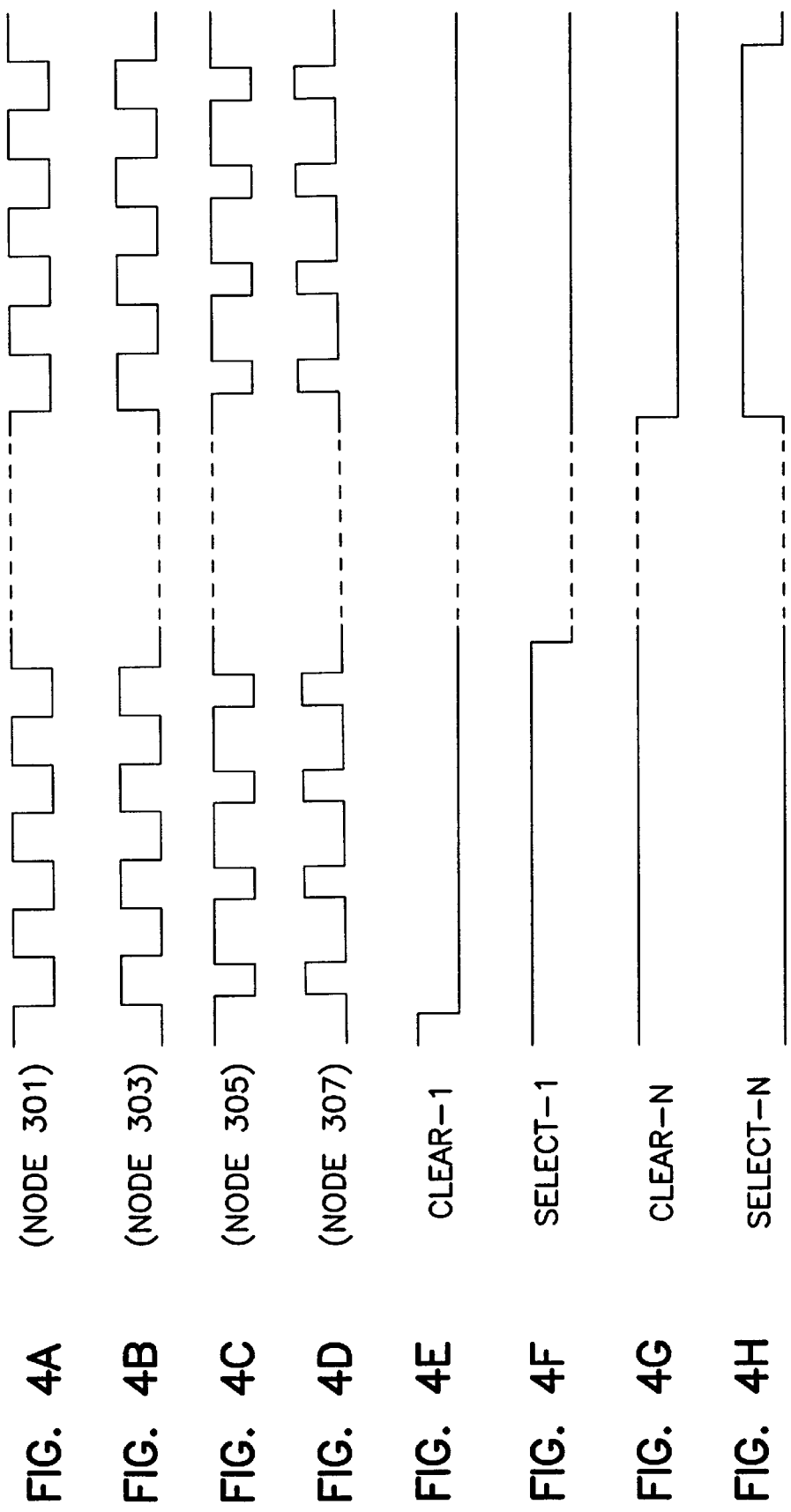

MULTIPLEXED PHASE DETECTOR

CROSS REFERENCE TO RELATED CASES

This application is related to the following commonly assigned, co-pending applications:

Application Ser. No. 09/478,486, entitled "PHASE DETECTOR" and filed on Jan. 6, 2000 (the '044 Application); and Application Ser. No. 09/478,762, entitled "ESTIMATION OF ERROR ANGLE IN ULTRASOUND FLOW MEASUREMENT" and filed on Jan. 6, 2000 (the '045 Application);

The '044 and '045 Applications are incorporated herein by reference.

NOTICE OF FEDERALLY SPONSORED RESEARCH

Portions of this invention may have been developed under Contract No. 1 R43 HL62803-01A1, awarded by the National Institutes of Health. Therefore, the U.S. Government may have a paid-up license in portions of this invention and the right, in limited circumstances, to require the patent owner to license others on reasonable terms as provided for by the terms of the contract.

TECHNICAL FIELD OF THE INVENTION

The present invention relates generally to the field of electronic circuits and, in particular, to a multiplexed phase detector.

BACKGROUND

Phase detectors detect or measure the relative phase of two signals with respect to each other, and are used in a wide variety of electronic systems. For example, a phase detector is a fundamental building block for a phase lock loop (PLL) found in many electronic systems. A PLL is particularly useful in demodulating radio frequency (RF) signals in, for example, an FM radio receiver.

A PLL is a circuit that causes a particular system to track with another system. More particularly, a PLL is a circuit that synchronizes an output signal (generated by an oscillator, e.g., a voltage controlled oscillator) with a reference or input signal in frequency as well as in phase. A typical PLL includes three main building blocks: a phase detector, a loop filter and a voltage (or current) controlled oscillator. The phase detector receives the reference or input signal as well as the output of the voltage controlled oscillator. The phase detector measures the phase difference between the input signal and the output signal of the voltage controlled oscillator. The phase difference acts as an error signal that is fed to the voltage controlled oscillator via the loop filter. When, the phase detector detects zero, or very small, phase error between the input or reference signal and the output of the oscillator, the PLL is said to be locked.

Common types of phase detectors include analog multiplier circuits such as the Gilbert cell and ring diode mixer topologies. These phase detectors typically accept sinusoidal input signals. Other phase detectors accept digital input signals. For example, exclusive OR gate and RS Flip-Flop phase detectors fall into this category. The detectors produce a duty cycle modulated output whose average value is proportional to the phase difference. A last type of detector is the Sequential Phase/Frequency Detector. This type of detector produces two outputs, the first (second) labeled as up (down). These two outputs are individually duty cycle modulated depending on which input is leading and the magnitude of the phase difference.

Phase detectors are used in a number of conventional applications requiring continuous measurement of phase error control, e.g., a Voltage Controlled Oscillator (VCO). Other applications include using a phase detector to measure the change in phase in a Phase Shifted Keying (PSK) communications system where the digital data is encoded in the phase of the transmitted signal. These examples show applications where the measurement of phase is important, but not necessarily the precise measurement of phase. An application, which requires a precise measurement of phase, is a Transit Time flow meter.

A Transit Time flow meter estimates volumetric flow by measuring the phase difference between bursts of ultrasound traveling upstream, and downstream paths across a tube with moving fluid. The phase difference is dependent on the volumetric flow when the entire tube or vessel is illuminated with the sound waves. Papers published by Craig Hartley, Ph.D., or Cor Drost, Ph.D., explain that the moving fluid causes the time required by the sound waves to travel across the vessel to be different for an upstream and downstream path when the fluid is moving. In other words, when the same signal is transmitted on the upstream and downstream paths, a phase difference is introduced between the two received signals.

Transonics Systems Inc., a commercial supplier of Transit-Time flow measurement equipment, measures the phase shift with an analog multiplier. This multiplies the received ultrasound signal with the signal from a master oscillator and measures the phase difference between the two input signals. The measurement cycle is repeated on the opposite direction and the phase measurements are subtracted to produce the phase shift between the upstream and downstream paths. The phase difference measured is then proportional to the volumetric flow at that point in time. A limitation of this phase detection method requires a long burst of ultrasound be transmitted from one transducer to the other, along the upstream or downstream path, with a duration long enough to allow the analog multiplier and the low pass filter time to settle on the phase value.

Crystal Biotech, Inc. (CBI) uses another method to measure phase shifts in a Transit Time flow meter. CBI simultaneously transmits a short burst of ultrasound from two transducers in a probe and compares the phase shift of the received ultrasound bursts from the upstream and downstream paths directly to each other. The CBI Transmit Time flow meter includes a digital circuit with a single output. This output signal has its duty cycle modulated by the phase difference. This single modulated output switches on and off a current source with a capacitor as its load with a selectable number of pulses. The current source is switched on and off and the capacitor is used to store the charge, which is proportional to the time the current source is on. The charge on the capacitor generates a voltage, which is proportional to the phase shift between the two input signals. One shortcoming of the CBI device is that the portion of the signal representing the change in phase is a small percentage of the total charge on the capacitor. Therefore, it is difficult to reliably measure the small phase changes generated by the CBI Transit Time flow meter.

For the reasons stated above, and for other reasons stated below which will become apparent to those skilled in the art upon reading and understanding the present specification, there is a need in the art for a phase detector that provides a more rapid and accurate measure of the phase difference between two signals.

SUMMARY

The above mentioned problems with phase detectors and other problems are addressed by the present invention and will be understood by reading and studying the following specification. A phase detector is described which selects from a number of input signals and generates at least one output signal based on a phase difference between the selected input signals using duty cycle modulation.

In one embodiment, a method for detecting a phase difference is provided. The method includes selecting first and second input signals from a plurality of pairs of input signals. The method further includes modulating a duty cycle of first and second intermediate signals from a first duty cycle based on a phase difference between the first and second input signals. The method also includes creating a differential signal based on the modulated duty cycles of the first and second intermediate signals that is related to the phase difference between the first and second input signals.

BRIEF DESCRIPTION OF THE DRAWINGS

FIGS. 4A through 4H are timing diagrams that illustrate one embodiment of a process for controlling a phase detector according to the teachings of the present invention.

DETAILED DESCRIPTION

The following detailed description refers to the accompanying drawings which form a part of the specification. The drawings show, and the detailed description describes, by way of illustration specific illustrative embodiments in which the invention may be practiced. These embodiments are described in sufficient detail to enable those skilled in the art to practice the invention. Other embodiments may be used and logical, mechanical and electrical changes may be made without departing from the scope of the present invention. The following detailed description is, therefore, not to be taken in a limiting sense.

I. First Embodiment of a Multiplexed Phase Detector

Figure 1:
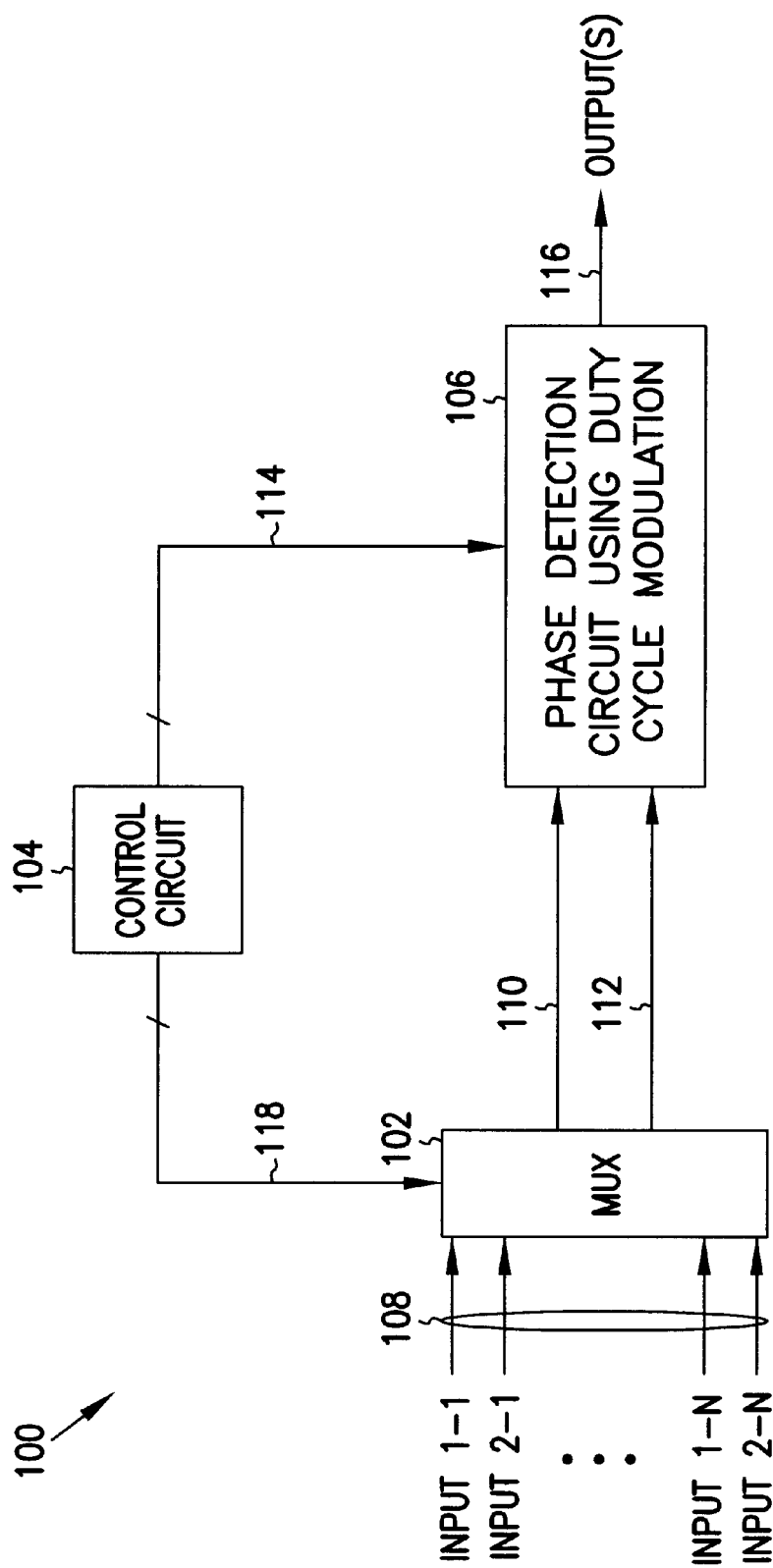
FIG. 1 is a block diagram of an embodiment of a phase detector constructed according to the teachings of the present invention.

FIG. 1 is a block diagram of a first embodiment of a multiplexed phase detector, indicated generally at 100, constructed according to the teachings of the present invention. Phase detector 100 includes multiplexer 102, control circuit 104, and phase detection circuit 106 that uses duty cycle modulation to generate at least one output signal that represents the phase difference between at least two input signals.

Multiplexer 102 receives input signals for multiplexed phase detector 100. Multiplexer 102 includes a number of inputs 108. Inputs 108 receive pairs of input signals labeled INPUT 1-1, 2-1, . . . , INPUT 1-N, 2-N. Multiplexer 102 is coupled to control circuit 104 and receives a selection signal from control circuit 104. Based on this selection signal, multiplexer 102 provides one of the pair of input signals 108 to phase detection circuit 106 by coupling one of signals INPUT 1-1, . . . , INPUT 1-N to input 110 of phase detection circuit 106 and coupling one of signals INPUT 2-1, . . . , INPUT 2-N to input 112 of phase detection circuit 106. In another embodiment, multiplexer 102 is implemented as two multiplexers with a first multiplexer with N inputs coupled to receive input signals INPUT 1-1, . . . , INPUT 1-N and an output coupled to input 110 of phase detection circuit 106 and a second multiplexer with N inputs coupled to receive input signals INPUT 2-1, . . . , INPUT 2-N and an output coupled to input 112 of phase detection circuit 106.

Control circuit 104 is also coupled to phase detection circuit 106. Control circuit 104 provides selected control signals 114 to phase detection circuit 106 to control the generation of at least one output signal at output 116.

Phase detection circuit 106 processes input signals from multiplexer 102 in accordance with control signals from control circuit 104 to produce one or more output signals related to phase differences between pairs of signals at inputs 108. Phase detection circuit 106 uses duty cycle modulation as described in the '044 Application to generate signals that represent a phase difference in at least one pair of signals at inputs 108.

In one embodiment, the output of phase detection circuit 106 comprises a single output 116 that is related to the average of the phase difference between two or more pair of signals at inputs 108. In another embodiment, the output of phase detection circuit 106 comprises multiple outputs 116 that provide separate phase measurements for multiple pairs of input signals at inputs 108. In one embodiment, control circuit 104 provides control signals 114 to phase detection circuit 106 to sequentially detect phase differences between pairs of signals at inputs 108.

In operation, multiplexed phase detector 100 receives a number of input signals and produces at least one output signal that relates to a phase difference between a pair of the input signals 108.

Multiplexer 102 receives a number of input signals in pairs at inputs 108. Multiplexer 102 selects among the input signals at inputs 108 based on control signals 118 from control circuit 104. Multiplexer 102 provides the selected input signals to inputs 110 and 112 of phase detection circuit 106.

Based on the signals from control circuit 104, phase detection circuit 106 uses duty cycle modulation to generate at least one output signal 116 related to the phase difference between the input signals 110 and 112 from multiplexer 102. In one embodiment, phase detection circuit 106 generates first and second output signals 116 in succession that relate to phase differences between first and second pairs of input signals at inputs 108. In another embodiment, phase detection circuit 106 produces a single output signal 116 that relates to an average phase difference between two or more pair of input signals at inputs 108. In other embodiments, phase detection circuit 106 generates a number of outputs 116 that are related to phase differences between pairs of input signals at inputs 108.

II. Second Embodiment of a Multiplexed Phase Detector

Figure 2:
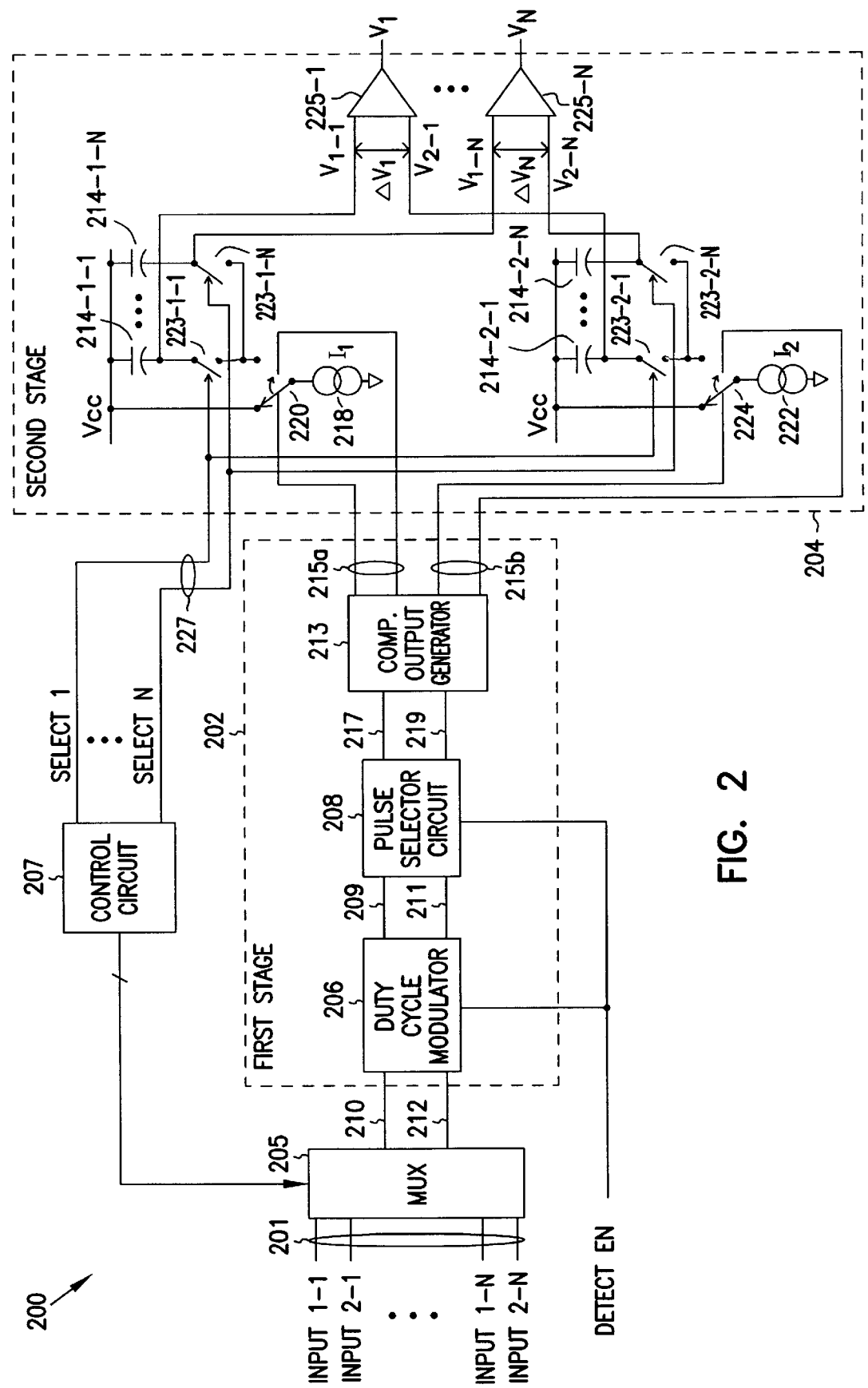
FIG. 2 is a block diagram of another embodiment of a phase detector constructed according to the teachings of the present invention.

FIG. 2 is a block diagram of an embodiment of a multiplexed phase detector indicated generally at 200 and constructed according to the teachings of the present invention. Phase detector 200 measures the phase difference or time shift between pairs of input signals 201, e.g., pairs of signals, INPUT 1-1, INPUT 1-2, . . . , and INPUT 1-N, INPUT 2-N.

As an overview, multiplexed phase detector 200 includes first and second stages 202 and 204, multiplexer (MUX) 205 and control circuit 207. Multiplexer 205 selects a pair of inputs from input signals 201 and presents the selected inputs to inputs 210 and 212 of first stage 202. First stage 202 uses duty cycle modulator 206 to modulate the duty cycle of intermediate signals at nodes 209 and 211 with the phase difference between the pair of signals selected by multiplexer 205. First stage 202 further selects a number of pulses from the duty cycle modulated signals to be further processed by second stage 204.

Second stage 204 uses the duty cycle modulated signals from first stage 202 to control switches that charge first and second capacitors of a pair of capacitors. Once charged, the voltages on the capacitors are related to the duty cycle of the duty cycle modulated signals. Since the duty cycles of the signals used to control the charging of the capacitors contain information about the phase difference between the selected input signals, the voltages on the capacitors, once charged, provide a differential voltage output that is related to the phase difference between the input signals. For example, in one embodiment, the differential voltage is proportional to twice the phase difference between the input signals.

In this embodiment, second stage 204 includes multiple pairs of capacitors that are selectively charged through switches based on the duty cycle modulated signals. In this manner, second stage 204 is operable measure the phase difference for multiple pairs of input signals in succession. In some embodiments, these measurements are generated in rapid succession thereby allowing portions of the circuitry to be powered down for longer periods of time between measurements this improving the suitability of this phase detector for implantable applications.

A. First Stage—Duty Cycle Modulation and Pulse Selection

First stage 202 operates on input signals selected by multiplexer 205 based on control signals from control circuit 207. First stage 202 modulates the duty cycle of intermediate signals and selects a number of pulses from the duty cycle modulated signals for further processing. First stage 202 includes duty cycle modulator 206 and pulse selector circuit 208.

Duty cycle modulator 206 includes first and second inputs 210 and 212. Duty cycle modulator 206 is designed to process square wave inputs. Thus, in one embodiment, optional comparators (not shown) are provided, when necessary, at inputs 210 and 212, respectively, to convert the signals selected by multiplexer 205 to square wave format.

The selected input signals from signals 201 are each periodic signals that have substantially the same frequency and the same nominal duty cycle, e.g., a fifty percent duty cycle. In one embodiment, the high logic level pulses ("the active period of the signal") in the respective square waves of signals provided to duty cycle modulator 206 are substantially one half of the period of the signals. The signals provided to duty cycle modulator 206 may, however, have different phase, e.g., one of the signals in the pair may be shifted in time with respect to the other signal.

I. Duty Cycle Modulation

Duty cycle modulator 206 uses the phase difference between the signals from multiplexer 205, if any, to generate intermediate signals at nodes 209 and 211. The signals at nodes 209 and 211 have the same frequency as the signals selected by multiplexer 205 but their duty cycles are modulated from the nominal, e.g., fifty percent duty cycle, based on the phase difference between the signals selected by multiplexer 205. For example, in one embodiment, the duration of the high logic level pulses in the signal at node 209 is increased by the duration of the phase difference between the signals from multiplexer 205 and the duration of the high logic level pulses in the signal at node 211 is decreased by the same amount.

As described with respect to FIGS. 6A through 6K in the '044 Application, in one embodiment, the signals at nodes 209 and 211 are created based on the rising and falling edges of signals selected by multiplexer 205. Advantageously, the use of both rising and falling edges in performing phase modulation reduces problems with cross-over when the signals selected by multiplexer 205 are close to phase alignment.

II. Pulse Selection

Pulse selector circuit 208 selects pulses from signals at nodes 209 and 211 to be used by second stage 204 to determine the phase difference between signals selected by multiplexer 205. Pulse selector circuit 208 can be programmed as to the number of pulses to select and which pulses within the pulse trains at nodes 209 and 211 to select. In one embodiment, pulse selector 208 essentially selects the pulses to be used by counting pulses after a time delay from the transmission of signals that created the signals selected by multiplexer 205. This selection can be based on data stored in a non-volatile memory associated with pulse selector 208 that downloads data for selected fixed time delays based on the operating environment of phase detector 200.

For example, in one embodiment, the signals selected by multiplexer 205 comprise signals derived from 16 cycles of a 10 MHZ ultrasonic waveform used in a transit time flow meter. Pulse selector circuit 208 is programmed to select, e.g., the eighth pulse in each of the signals at nodes 209 and 211. These pulses are used by second stage 204 to determine the phase difference between the signals selected by multiplexer 205. Advantageously, these single pulses from the signals at nodes 209 and 211 provide sufficient information to provide a measure of the phase difference between the signals. By using a small number of pulses, phase detector 200 can be used in low power implementations such as implanted medical devices.

Alternatively, pulse selector circuit 208 can select a larger number of specified pulses from the signals at nodes 209 and 211, e.g., four pulses from the middle of the pulse trains. In this case, second stage 204 advantageously averages the information on the phase difference for the four pulses to provide a measure of the phase difference detected by multiplexed phase detector 200 for each pair of signals selected by multiplexer 205. In this manner, minor variations in phase difference from pulse-to-pulse are averaged out by second stage 204.

It is noted that pulses located near the middle of the pulse trains of signals at nodes 209 and 211 may provide a more accurate measure of the phase difference between the signals selected by multiplexer 205.

Pulse selector circuit 208 provides the selected pulses from the signals at nodes 209 and 211 to complimentary output generator 213 at nodes 217 and 219, respectively. Complementary output generator 213 generates two pair of complementary outputs 215a and 215b, respectively. Complementary outputs 215a comprise the signal at node 217 and its complement. Complementary outputs 215b comprise the signal at node 219 and its complement. Complementary outputs 215a and 215b are provided to second stage 204.

Figure 5:
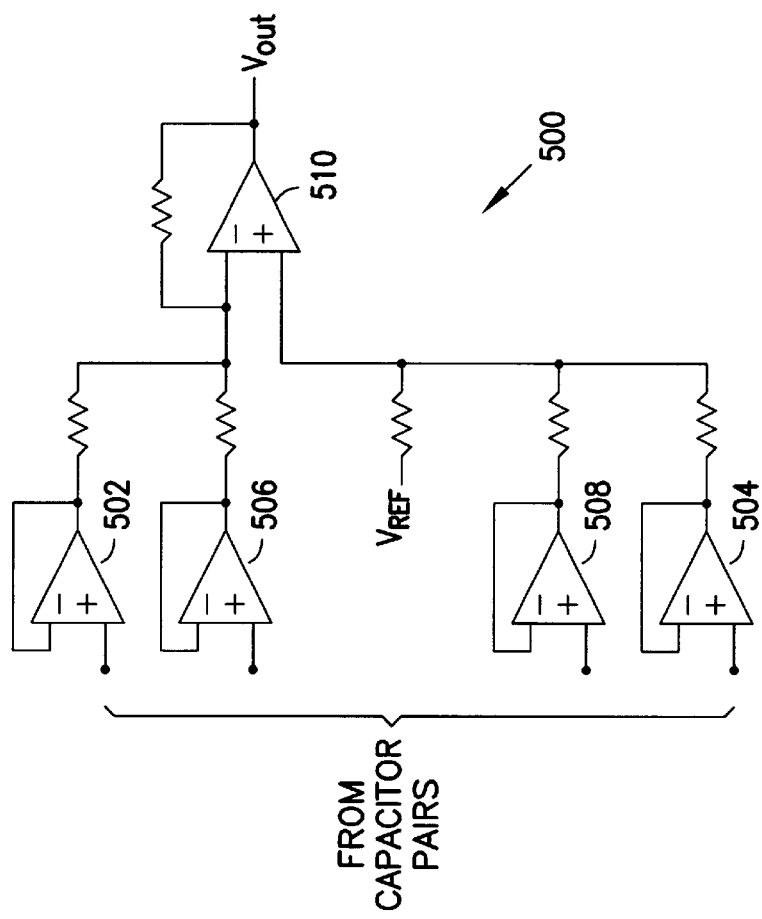
Figure 9:
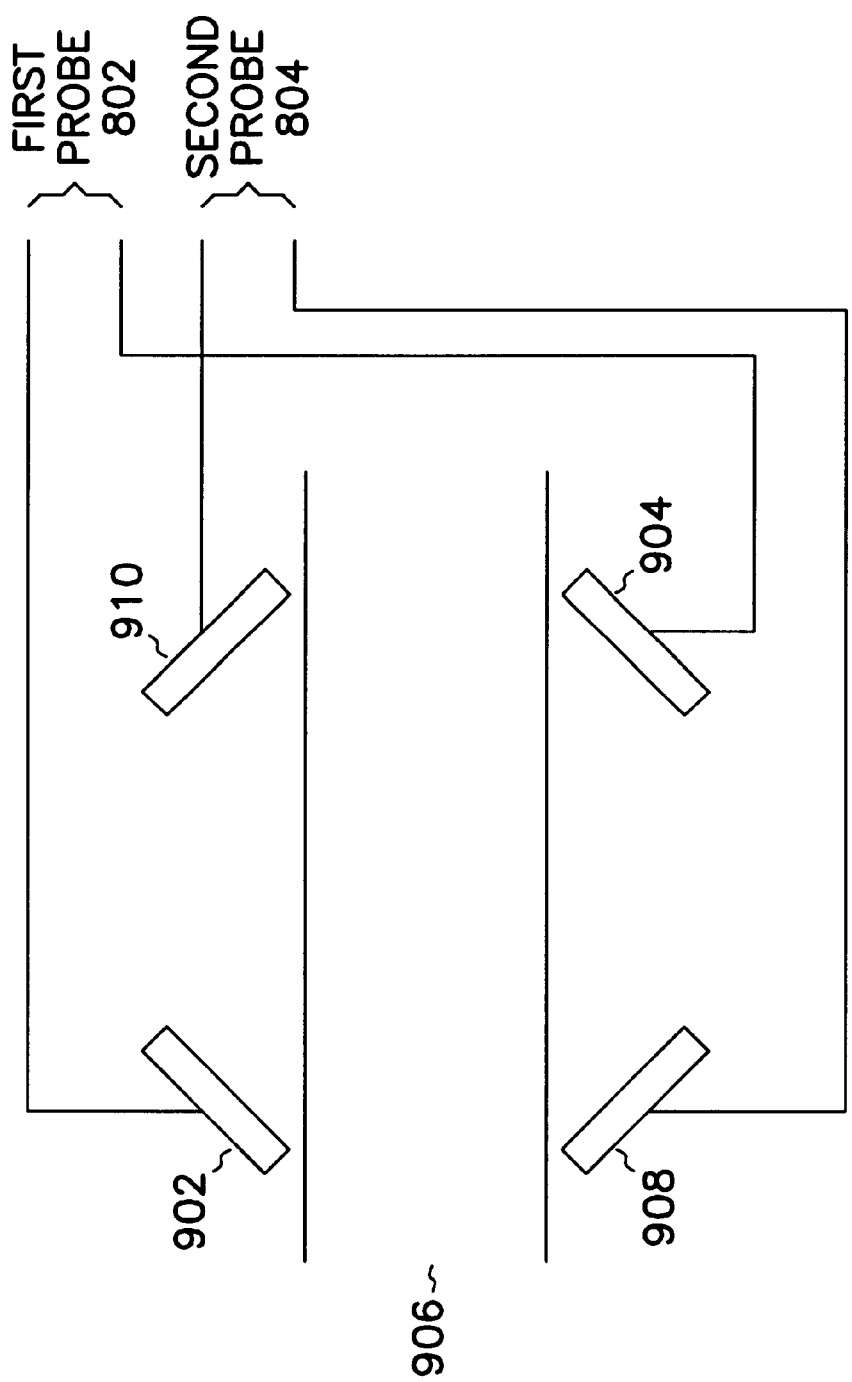
FIG. 9 is a block diagram of an embodiment of a probe for a transit time flow meter according to the teachings of the present invention.

Embodiments of a pulse selector circuit are described with respect to FIGS. 5 and 9 of the '044 Application. The circuits of FIGS. 5 and 9 of the '044 Application are provided by way of example and not by way of limitation..

A signal labeled DETECT EN is also provided to both duty cycle modulator 206 and pulse selector circuit 208. The DETECT EN signal enables phase detector 200 to operate.

B. Second Stage—Generation of Voltage Related to Phase Difference

Second stage 204 uses the complementary outputs 215a and 215b from first stage 202 to create two or more voltages, labeled $V_1, \ldots, V_N$, that are related to the phase difference between the selected input signals. Second stage 204 includes a plurality of pairs of first capacitors 214-1-1, . . . , 214-1-N and second capacitors 214-2-1, . . . , 214-2-N, respectively. First capacitors 214-1-1,. . . , 214-1-N are selectively coupled to current source 218 through switch 220. Switch 220 is controlled based on complementary outputs 215a of first stage 202. Similarly, second capacitors 214-2-1, . . . , 214-2-N are selectively coupled to current source 222 through switch 224. Switch 224 is controlled based on complementary outputs 215b of first stage 202.

First capacitors 214-1-1, . . . , 214-1-N are selectively and controllably coupled to switch 220 through switches 223-1-1, . . . , 223-1-N, respectively, under the control of signals 227 from control circuit 207. Similarly, second capacitors 214-2-1, . . . , 214-2-N are selectively coupled to switch 224 through switches 223-2-1, . . . , 223-2-N, respectively, under the control of signals 227 from control circuit 207. Essentially, control circuit 207 allows one pair of capacitors at a time to be coupled to switches 220 and 224 based on the selected pair of input signals 201. Thus, each pair of capacitors is used to measure a phase difference between a pair of input signals 201.

For sake of clarity in FIG. 2, a mechanism for clearing the voltage on capacitors 214-1-1, . . . , 214-1-N and 214-2-1, . . . , 214-2-N is not shown. However, one of ordinary skill in the art understands that switches such as switches 325-1, . . . , 325-N and 335-1, . . . , 335-N of FIG. 3 may be included to perform this function.

Second stage 204 includes a number of amplifiers 225-1, . . . , 225-N that are coupled to pairs of capacitors. For example, amplifier 225-1 is coupled to first and second capacitors 214-1-1 and 214-2-1. Similarly, amplifier 225-N is coupled to capacitors 214-1-N and 214-2-N. Amplifiers 225-1, . . . , 225-N provide outputs $V_1, \ldots, V_N$ for multiplexed phase detector 200. Advantageously, second stage 204 allows multiplexed phase detector 200 to measure phase differences between pairs of input signals 201 in succession.

C. Operation

In operation, multiplexed phase detector 200 receives signals 201 and determines the phase difference, if any, between signals in selected pairs of input signals 201. Initially, multiplexer 205 selects a pair of input signals under the control of control circuit 207. Duty cycle modulator 206 creates intermediate signals at nodes 209 and 211 with duty cycle modulation based on the phase or phase difference between selected input signals 201. Pulse selector circuit 208 then selects a number of pulses in the pulse trains of the intermediate signals and provides those pulses to complementary output generator 213 to generate two pair of complementary outputs 215a and 215b for second stage 204.

At second stage 204, the complementary signals 215a and 215b control the operation of switches 220 and 224, respectively, to selectively charge a pair of capacitors selected by control circuit 207, e.g., first capacitor 214-1-1 and second capacitor 214-2-1, based on the phase difference between the selected input signals 201 as described in the '044 Application. The voltages on the capacitors 214-1-1 and 214-2-1 are provided to amplifier 225-1 to provide one output signal.

Additional pairs of input signals in input signal 201 are sequentially selected by multiplexer 205 and additional outputs are generated by second stage 204.

III. Another Embodiment of a Second Stage

Figure 3:
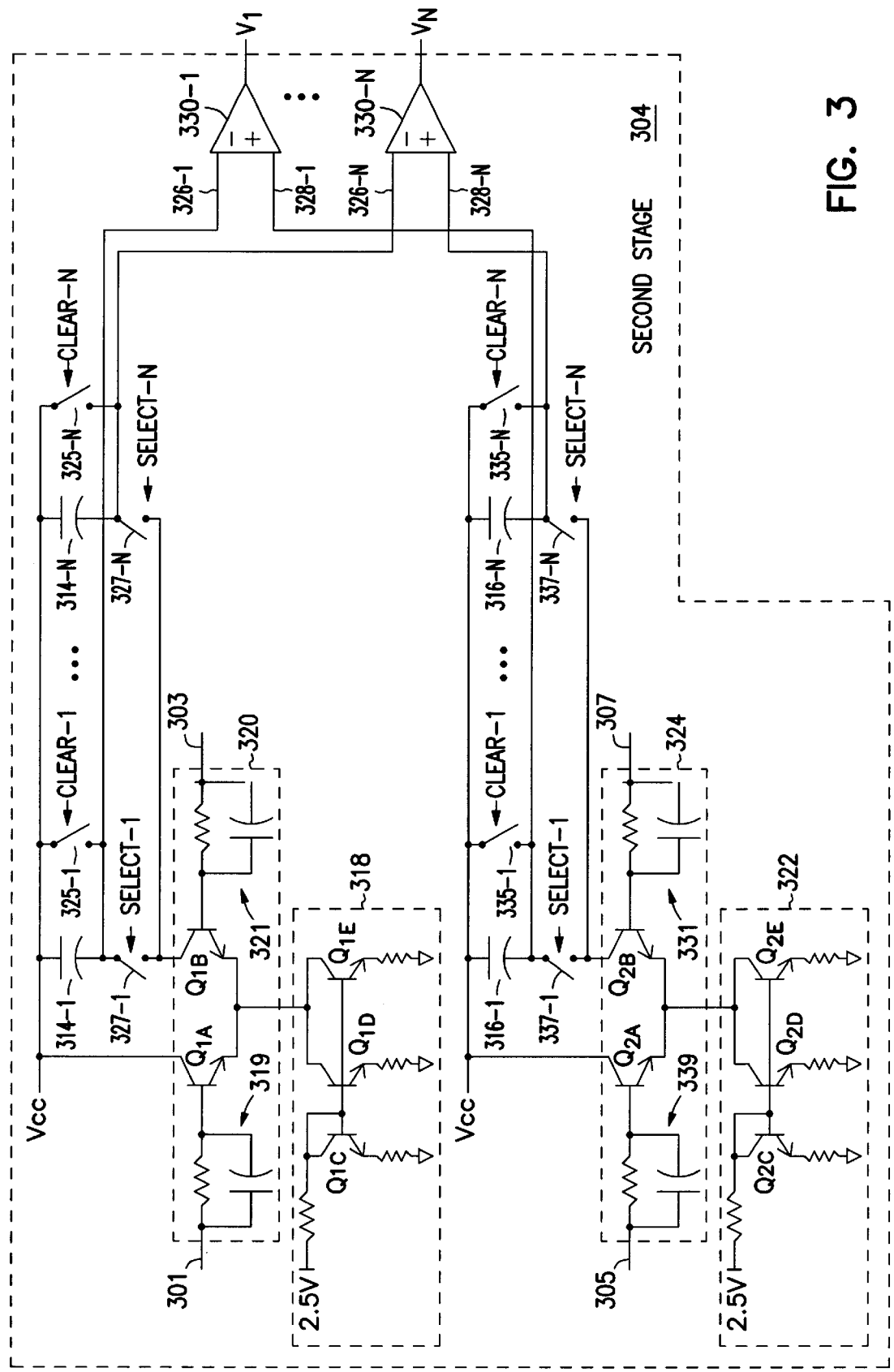
FIG. 3 is a schematic diagram of an embodiment of a portion of a phase detector constructed according to the teachings of the present invention.

FIG. 3 is a schematic diagram of another embodiment of a second stage, indicated generally at 304, for use in a multiplexed phase detector according to the teachings of the present invention. Second stage 304 receives first complementary input signals at nodes 301 and 303, and second complementary input signals at nodes 305 and 307 from, for example, first stage 202 of FIG. 2. Second stage 304 creates a number of outputs, labeled $V_1, \ldots, V_N$. The outputs, $V_1, \ldots, V_N$ are related to the. phase difference between selected input signals to the multiplexed phase detector.

Second stage 304 includes a plurality of pair of capacitors. Each pair of capacitors includes one of first capacitors 314-1, . . . , 314-N and one of second capacitors 316-1, . . . , 316-N. First capacitors 314-1, . . . , 314-N are selectively coupled to current source 318 through switch 320. First capacitors 314-1, . . . , 314-N are coupled to input 326-1, . . . , 326-N of instrumentation amplifier 330-1, . . . , 330-N, respectively.

In this embodiment, current source 318 includes transistors $Q_{1C}, Q_{1D}, Q_{1E}$ that are coupled to form a current mirror. Optional resistors are coupled to the emitters of transistors $Q_{1C}, Q_{1D}, Q_{1E}$ to provide invariance to temperature change and to variations in emitter-base voltage. It is noted that the current mirror in this embodiment uses a 2.5 volt reference voltage to create the constant current for switch 320. Advantageously, this reference voltage reduces changes caused by fluctuations in the power supply $V_{CC}$. It is also noted that the value of the reference voltage in FIG. 3 can be varied as necessary for a particular application. The values shown are provided by way of illustration and not by way of limitation.

Switch 320 comprises a differential amplifier formed from transistors $Q_{1A}$ and $Q_{1B}$. Transistors $Q_{1A}$ and $Q_{1B}$ may be formed on the same die, e.g., using transistor arrays, to reduce differences in the emitter-base voltage due to temperature and other factors. Further, transistors $Q_{1A}$ and $Q_{1B}$ should be fast enough to allow even small phase differences on the order of 0.1 nanoseconds or less to be resolved.

The complementary input signals at nodes 301 and 303 are provided to transistors $Q_{1A}$ and $Q_{1B}$ through RC networks 319 and 321, respectively.

Second stage 304 also includes switches 325-1, ..., 325-N to clear the voltage on capacitors 314-1, ..., 314-N, respectively. Switches 325-1, ..., 325-N are coupled in parallel with capacitors 314-1, ..., 314-N, respectively, and comprise, for example, analog switches with control inputs coupled to signals labeled CLEAR-1, ..., CLEAR-N. When the signal CLEAR-1 is raised to a high voltage level, for example, switch 325-1 is closed so as to clear the voltage on capacitor 314-1. When the signals CLEAR-1, ..., CLEAR-N are maintained at a low level, the voltage on the associated capacitors 314-1, ..., 314-N are changed based on the complementary signals provided to nodes 301 and 303.

Second stage 304 also includes switches 327-1, ..., 327-N that selectively couple associated capacitors 314-1, ..., 314-N to switch 320 based on control signals SELECT-1, ..., SELECT-N. This allows a number of pairs of input signals to be processed in succession, storing signals representing a phase difference between a pair of input signals on a selected pair of capacitors.

Switches 327-1, ..., 327-N further allow the voltage on associated capacitors 314-1, ..., 314-N, respectively, to be held at a level so that the output of associated amplifiers 330-1, ..., 330-N can be read. Since switch 320 is formed with bipolar junction transistors, switch 320 would draw a small current even when the switch is off. Thus, switches 327-1, ..., 327-N are added to prevent leakage from capacitors 314-1, ..., 314-N that would destroy the integrity of the value stored on capacitors 314-1, ..., 314-N.

Second capacitors 316-1, ..., 316-N are coupled to current source 322 through switch 324. Capacitors 316-1, ..., 316-N are coupled to input 328-1, ..., 328-N of instrumentation amplifiers 330-1, ..., 330-N.

In this embodiment, current source 322 includes transistors $Q_{2C}$, $Q_{2D}$, $Q_{2E}$ that are coupled to form a current mirror. Optional resistors are coupled to the emitters of transistors $Q_{2C}$, $Q_{2D}$, $Q_{2E}$ to provide invariance to temperature change and to variations in emitter-base voltage. It is noted that the current mirror in this embodiment uses a 2.5 volt reference voltage to create the constant current for switch 324. Advantageously, this reference voltage reduces changes caused by fluctuations in the power supply $V_{CC}$. It is also noted that the value of the reference voltage and the value of the resistors shown in FIG. 3 can be varied as necessary for a particular application.

Current sources 318 and 322 may be matched current sources so as to provide substantially the same current for capacitors 314-1, ..., 314-N and 316-1, ..., 316-N. Alternatively, current sources 318 and 322 may be replaced with a single current source which provides current for both switches 320 and 324. Further, first capacitors 314-1, ..., 314-N have substantially the same value as their corresponding second capacitors 316-1, ..., 316-N.

Switch 324 comprises a differential amplifier formed from transistors $Q_{2A}$ and $Q_{2B}$. Transistors $Q_{2A}$ and $Q_{2B}$ may be formed on the same die, e.g., using transistor arrays, to reduce differences in the emitter-base voltage due to temperature and other factors. Further, transistors $Q_{2A}$ and $Q_{2B}$ should be fast enough to allow even small phase differences on the order of 0.1 nanoseconds or less to be resolved.

The complementary input signals at nodes 305 and 307 are provided to transistors $Q_{2A}$ and $Q_{2B}$ through RC networks 339 and 331, respectively.

Second stage 304 also includes switches 335-1, ..., 335-N to clear the voltage on second capacitors 316-1, ..., 316-N, respectively. Switches 335-1, ..., 335-N are coupled in parallel with capacitors 316-1, ..., 316-N, respectively, and comprise, for example, analog switches with control inputs coupled to signals labeled CLEAR-1, ..., CLEAR-N. When the signal CLEAR-1 is raised to a high voltage level, for example, switch 335-1 is closed so as to clear the voltage on capacitor 316-1. When the signals CLEAR-1, ..., CLEAR-N are maintained at a low level, the voltage on the associated capacitors 316-1, ..., 316-N are changed based on the complementary signals provided to nodes 305 and 307.

Switches 337-1, ..., 337-N further allow the voltage on associated capacitors 316-1, ..., 316-N, respectively, to be held at a level so that the output of associated amplifiers 330-1, ..., 330-N can be read. Since switch 324 is formed with bipolar junction transistors, switch 324 would draw a small current even when the switch is off. Thus, switches 337-1, ..., 337-N are added to prevent leakage from capacitors 316-1, ..., 316-N that would destroy the integrity of the value stored on capacitors 316-1, ..., 316-N.

Stray capacitance and leakage current should be reduced at the junction of capacitors 314-1, ..., 314-N and 316-1, ..., 316-N with the collectors of transistors $Q_{1B}$ and $Q_{2B}$ since the voltage on these capacitors directly affects the measurement of the phase difference by second stage 304. This includes the capacitance on the input to switches 320 and 324.

In operation, second stage 304 generates a plurality of output signals, $V_1$, ..., $V_N$ that are proportional to the phase difference between signals in selected pairs of input signals. Second stage 304 receives two pair of complementary signals at nodes 301, 303, 305 and 307.

The complementary signals at nodes 301 and 303 control the operation of switch 320 and the complementary signals at nodes 305 and 307 control the operation of switch 324 to selectively charge a pair of selected capacitors, e.g., first capacitor 314-1 and second capacitor 316-1, based on the phase difference between the input signals as described in the '044 Application. The voltage on the capacitors 314-1 and 316-1 is provided to amplifier 330-1 to provide one output signal.

Additional pairs of input signals are sequentially selected and outputs are generated by second stage 204.

FIGS. 4A–4H provide examples of signals used in the operation of second stage 304. FIGS. 4A and 4B represent a first pair of complementary inputs provided to nodes 301 and 303, respectively. FIGS. 4C and 4D represent a second pair of complementary inputs provided to nodes 305 and 307, respectively.

FIG. 4E is an example of the signal CLEAR-1 that is reduced to a low logic level provided to switches 325-1 and 335-1 just prior to the first train of pulses in FIGS. 4A–4D. This allows capacitors 314-1 and 316-1 to be clear and ready to be charged based on the complementary inputs.

FIG. 4F is an example of the signal SELECT-1 provided to switches 327-1 and 337-1. Signal SELECT-1 is maintained at a high logic level through the first set of pulses in the complementary inputs of FIGS. 4A–4D. This allows capacitors 314-1 and 316-1 to be charged based on the phase difference to be measured by second stage 304.

In a similar manner, FIGS. 4G and 4H are examples of signals CLEAR-N and SELECT-N. The CLEAR-N signal is brought low just prior to the $N^{th}$ pulse train to allow capacitor 314-N and 316-N to be charged from a clear state. The SELECT-N signal of FIG. 4G is brought to a high logic level for the duration of the $N^{th}$ pulse train to allow capacitors 314-N and 316-N to be selectively charged based on the inputs shown in FIGS. 4A–4D.

IV. Embodiments of Optional Output Circuits for a Phase Detector

Figure 6:
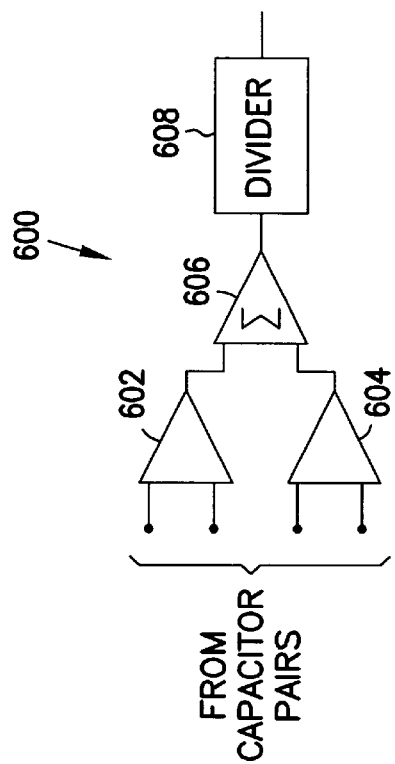
FIGS. 5, 6, and 7 are schematic diagrams of embodiments of an output portion of a phase detector according to the teachings of the present invention.
Figure 7:
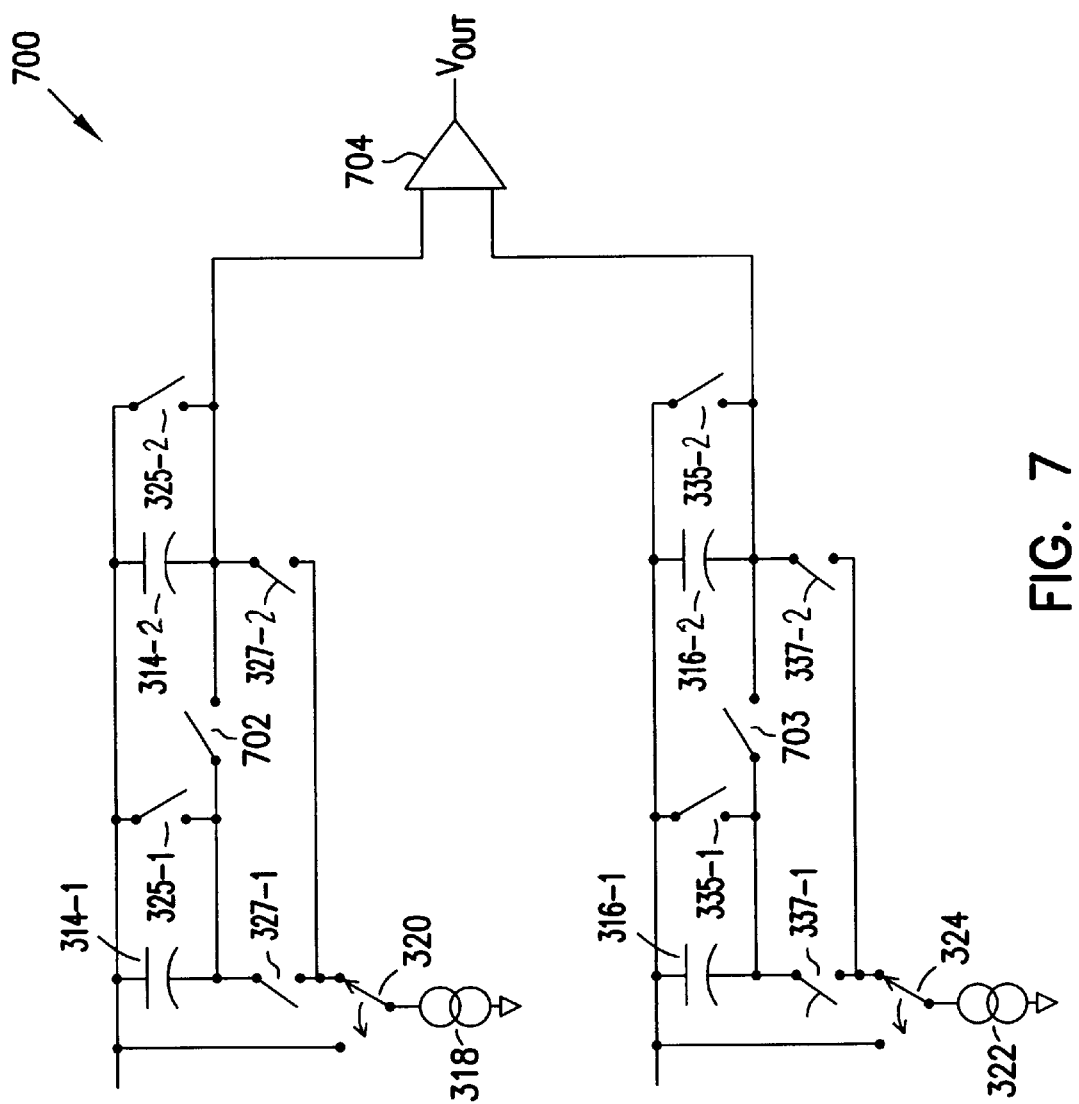

FIGS. 5, 6, and 7 are schematic diagrams of embodiments of output circuits for a phase detector according to the teachings of the present invention. Each of these embodiments is described in terms of use with second stage 304 of FIG. 3. However, it is understood that these output circuits can be used in conjunction with other embodiments of a multiplexed phase detector that uses duty cycle modulation.

FIG. 5 is a schematic diagram that illustrates an output circuit indicated generally at 500 and constructed according to the teachings of the present invention. Output circuit 500 operates to effectively add a measured phase difference between a pair of input signals with a measured phase difference between one or more other pair of input signals. In this embodiment, output circuit 500 adds two phase difference measurements.

Output circuit 500 includes buffers that are coupled to receive signals from capacitors that have been charged based on duty cycle modulated signals. First and second buffers 502 and 504 are coupled to a first pair of capacitors that are charged based on a first pair of duty cycle modulated signals. Third and fourth buffers 506 and 508 are coupled to a second pair of capacitors that are charged based on a second pair of duty cycle modulated signals.

Each of the buffers 502, 504, 506, and 508 are coupled through a resistor to amplifier 510. Amplifier 510 is configured to operate as an analog adder. The values for the resistors are selected based on the specific application of the phase detector, e.g., values are selected to produce an average of two or more values. A first input of amplifier 510 is coupled to buffers 502 and 506. A second input of amplifier 510 is coupled to buffers 504 and 508. As an option, a reference voltage, $V_{REF}$, is applied to the second input of amplifier 510 through a resistor.

In operation, first buffer 502 and second buffer 504 receive signals from their respective capacitors. These signals are provided to amplifier 510 as a first differential voltage. Subsequently, buffers 506 and 508 provide signals from their respective capacitors to amplifier 510 as a second differential voltage. Amplifier 510 adds the differential voltages and provides this as an output signal $V_{OUT}$.

FIG. 6 is a schematic diagram that illustrates an output circuit indicated generally at 600 and constructed according to the teachings of the present invention. Output circuit 600 operates to effectively average a measured phase difference between a pair of input signals with a measured phase difference between one or more additional pair of input signals. In this embodiment, output circuit 600 averages two phase difference measurements.

Output circuit 600 includes first and second amplifiers 602 and 604 that provide outputs that measure phase differences between first and second pairs of input signals. Amplifier 602 is coupled to receive signals from a first pair of capacitors that provide a differential voltage signal that is related to a phase difference between first and second input signals. Further, amplifier 604 is coupled to receive signals from a second pair of capacitors that provide a differential voltage signal that is related to a phase difference between third and fourth input signals.

Amplifiers 602 and 604 are coupled to the serial combination of summing amplifier 606 and divider 608. Summing amplifier 606 adds the outputs of amplifiers 602 and 604. Further, divider 608 divides the output of summing amplifier 606 by 2 to provide an output signal that is approximately, the average of the phase differences measured by amplifiers 602 and 604.

In another embodiment, additional amplifiers are coupled to inputs of summing amplifier 606 with the gains adjusted to produce an average value as the output of circuit 600. Alternatively, the gain of each amplifier is set to meet a specific output requirement.

FIG. 7 is a schematic diagram that illustrates a second stage with an output circuit indicated generally at 700 and constructed according to the teachings of the present invention. Second stage 700 operates to effectively average signals related to the phase difference between pairs of input signals. In this embodiment, second stage 700 averages two phase difference measurements. Second stage 700 is a modification of second stage 304 of FIG. 3. Thus, only the differences between the circuit of FIG. 3 and FIG. 7 are described in detail here.

In this embodiment, the output circuit of second stage 700 includes switches 702 and 703 and amplifier 704. Switch 702 couples capacitors 314-1 and 314-2 together once capacitors 314-1 and 314-2 are charged based on duty cycle modulated signals. This effectively averages the voltages on the capacitors. These average voltages are provided to an input of amplifier 704. A second input of amplifier 704 is coupled to capacitors 316-1 and 316-2. The voltages on capacitors 316-1 and 316-2 are averaged using switch 703.

In operation, a pair of phase measurements for first and second pairs of input signals are averaged and provided as an output signal by the output circuit of second stage 700. Once duty cycle modulated signals charge two pair of capacitors, switches 702 and 703 are closed. This averages the voltage on first capacitors 314-1 and 314-2 and averages the voltage on second capacitors 316-1 and 316-2. The average voltages are provided to amplifier 704 to provide a single output, $V_{OUT}$, that is related to the average of the phase difference for the two pair of input signals.

V. Embodiment of a Transit Time Flow Meter

Figure 8:
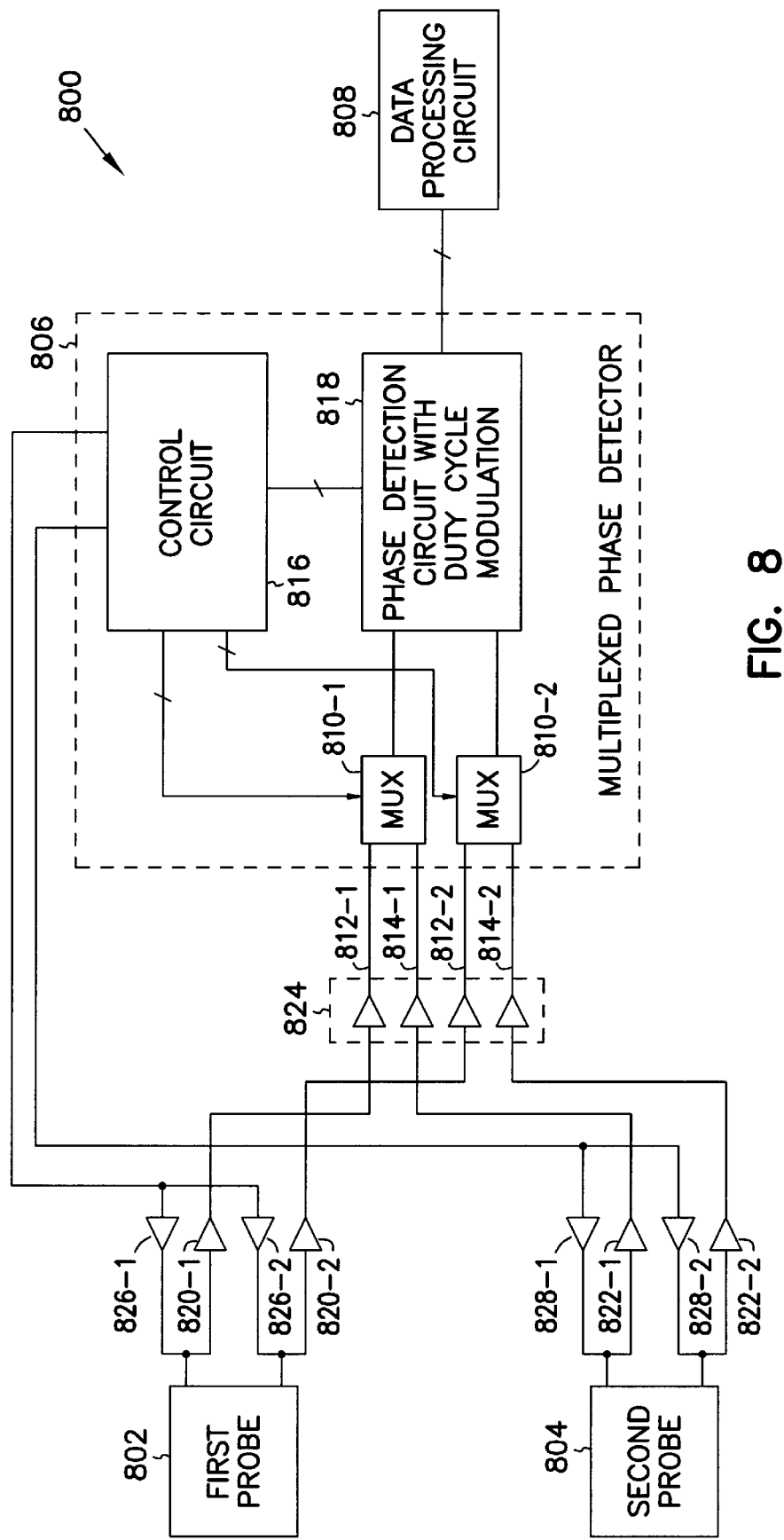
FIG. 8 is a block diagram of an embodiment of a transit time flow meter including a phase detector according to the teachings of the present invention.

FIG. 8 is a block diagram of a transit time flow meter indicated generally at 800 and constructed according to the teachings of the present invention. Flow meter 800 uses multiplexed phase detector 806 to measure a time-shift in ultrasonic signals transmitted through fluid in a conduit by first and second probes 802 and 804, respectively. The time shift is processed by. data processing circuit 808 to produce, for example, flow data, or a volumetric flow measurement.

Multiplexed phase detector 806 detects a phase difference or time-shift between a pair of input signals. Multiplexed phase detector 806 includes a pair of multiplexers 810-1 and 810-2. Multiplexer 810-1 is coupled to receive a pair of input signals at inputs 812-1 and 814-1. Input 812-1 is coupled to probe 802 and input 814-1 is coupled to second probe 804. Multiplexer 810-2 is coupled to receive a pair of input signals at inputs 812-2 and 814-2. Input 812-2 is coupled to first probe 802 and input 814-2 is coupled to second probe 804. The multiplexers 810-1 and 810-2 are each coupled to control circuits 816. Control circuit 816 provides selection signals to multiplexers 810-1 and 810-2. These control signals either select inputs 812-1 and 812-2 or inputs 814-1 and 814-2 to be provided as a pair of input signals to phase detection circuit 818. In one embodiment, control circuit 816 operates to provide the signals at inputs 812-1 and 812-2 followed by signals at inputs 814-1 and 814-2 in succession to phase detection circuit 818.

Phase detection circuit 818 uses duty cycle modulation to generate at least one output signal that is related to a time shift or phase difference between the selected input signals of multiplexers 810-1 and 810-2. Phase detection circuit 818 is constructed, for example, as described above with respect to any of FIGS. 1–7.

First probe 802 is coupled to multiplexed phase detector 806 at inputs 812-1 and 812-2 to provide a first time-shift measurement through receivers 820-1 and 820-2. Second probe 804 is coupled to multiplexed phase detector 806 at inputs 814-1 and 814-2 to provide a second time-shift measurement through receivers 822-1 and 822-2.

In one embodiment, comparators 824 are also provided at inputs 812-1, 812-2, 814-1, and 814-2. Comparators 824 adjust the signals from first probe 802 and second probe 804 to provide signals that are substantially square waves.

Control circuit 816 provides ultrasonic signals to first probe 802 and second probe 804 to create the time-shift signals provided to multiplexers 810-1 and 810-2. Control circuit 816 provides a first ultrasonic signal to first probe 802 through pulsers 826-1 and 826-2. Pulsers 826-1 and 826-2 provide bursts of ultrasonic energy to a pair of transducers of first probe 802. Similarly, control circuit 816 provides a second control signal to pulsers 828-1 and 828-2 for a pair of transducers of second probe 804.

One embodiment of first probe 802 and second probe 804 is shown by way of example in FIG. 9. As shown, first probe 802 includes a pair of transducers 902 and 904 that are located on opposite sides of conduit 906. Similarly, second probe 804 includes a pair of transducers 908 and 910 that are also located on opposite sides of conduit 906. Transducers 902, 904, 908, and 910 are disposed such that ultrasonic signals transmitted between the pairs of transducers form an X-pattern across a cross-section of conduit 906. It is noted that in other embodiments, first and second probes 802 and 804 comprise independent probes.

Flow meter 800 further includes data processing circuit 808 that is coupled to the output of phase detection circuit 818. In one embodiment, data processing circuit 808 includes circuitry that transmits the output of phase detection circuit 818 to a remote processor for processing to determine at least one flow rate. In other embodiments, data processing circuit 808 is fabricated in a common housing with multiplexed phase detector 806. In this embodiment, data processing circuit 808 uses the output of phase detection circuit 818 to calculate at least one flow rate. This data may be transmitted for use at a remote location.

In operation, flow meter 800 measures the flow of fluid in a conduit, e.g., the volumetric flow of the fluid in conduit 906 of FIG. 9. Initially, control circuits 816 provides a first ultrasonic signal to first probe 802 through pulsers 826-1 and 826-2. This ultrasonic signal contains a number of pulses that are transmitted from transducer 902 to transducer 904 and from transducer 904 to transducer 902. The received signals at transducers 902 and 904 are time-shifted due to the flow of fluid in conduit 906. Multiplexers 810-1 and 810-2 receive these time-shifted signals from receivers 820-1 and 820-2, respectively. Under the control of the signal from control circuit 816, multiplexers 810-1 and 810-2 provide these time-shifted signals to phase detection circuit 818. Phase detection circuit 818 uses duty cycle modulation to detect a phase difference between the signals selected by multiplexers 810-1 and 810-2. This provides a first measurement to be used in calculating flow rate.

Control circuit 816 then transmits the second ultrasonic signal to second probe 804 through pulsers 828-1 and 828-2. This ultrasonic signal also contains a number of pulses that are transmitted from transducer 908 to transducer 910 and from transducer 910 to transducer 908. The received signals at transducers 908 and 910 are time-shifted due to the flow of fluid in conduit 906. The multiplexers 810-1 and 810-2 receive from receivers 822-1 and 822-2, respectively, these time-shifted signals. Under the control of a signal from control circuit 816, multiplexers 810-1 and 810-2 provide these time-shifted signals to phase detection circuit 818. Phase detection circuit 818 uses duty cycle modulation to detect a phase difference (time-shift) between the signals selected by multiplexers 810-1 and 810-2. This provides a second measurement to be used in calculating flow rate.

Data processing circuit 808 uses the first and second measurements to calculate, e.g., a volumetric flow measurement. Alternatively, data processing circuit 808 transmits the first and second measurements to a remote processor for calculating one or more flow measurements.

VI. Embodiment of a Multiplexed Phase Lock Loop

Figure 10:
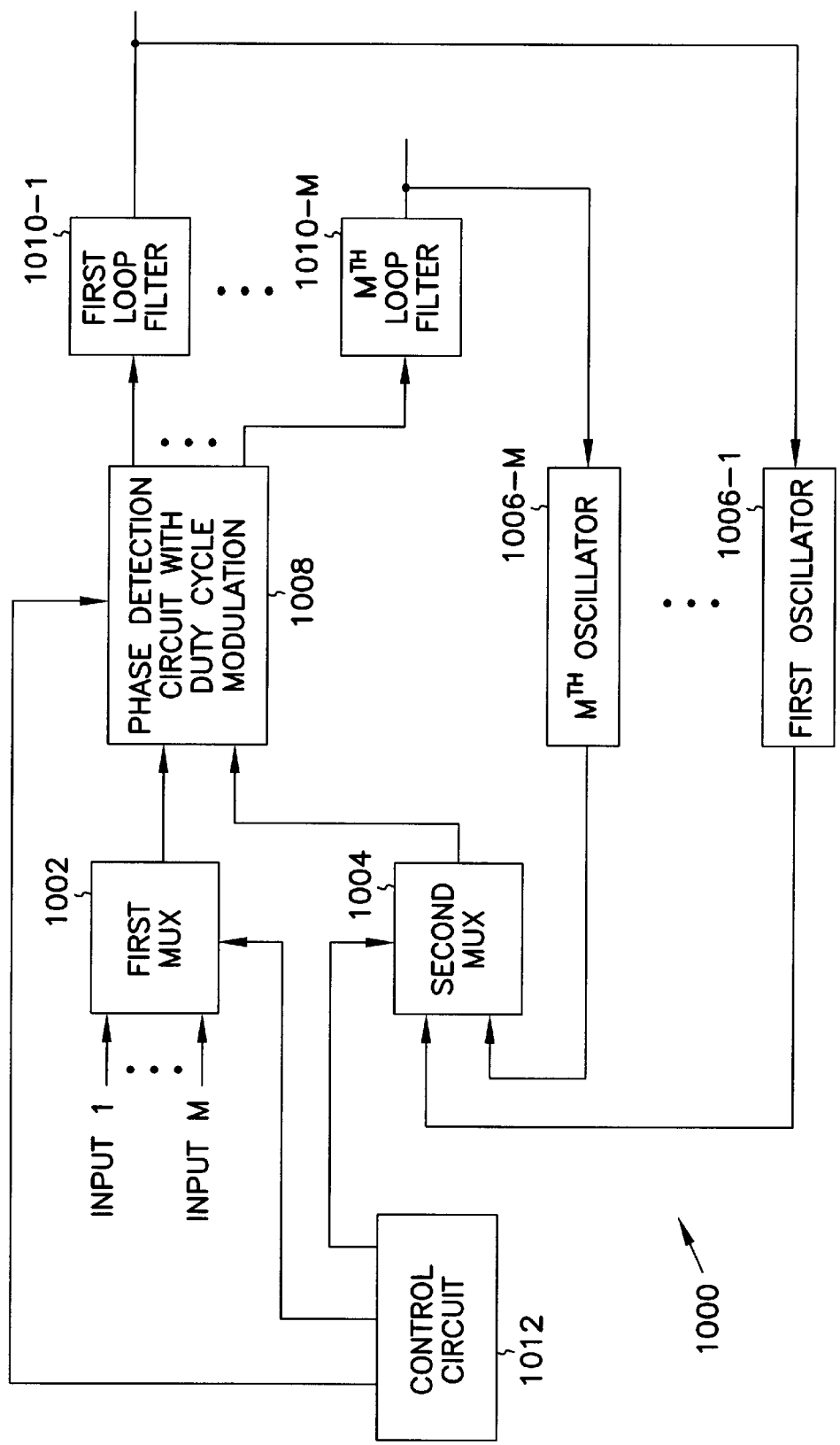
FIG. 10 is a block diagram of an embodiment of a multiplexed phase lock loop according to the teachings of the present invention.

FIG. 10 is a block diagram of multiplexed phase lock loop indicated generally at 1000 and constructed according to the teachings of the present invention. Phase lock loop 1000 includes first multiplexer 1002 that receives a plurality of inputs labeled INPUT 1, . . . , INPUT M. Phase lock loop 1000 also includes second multiplexer 1004 that receives inputs from oscillators 1006-1, . . . , 1006-M. First and second multiplexers 1002 and 1004 provide output signals to phase detection circuit 1008. Phase detection circuit 1008 uses duty cycle modulation to detect a phase difference between the signals from first and second multiplexers 1002 and 1004. In one embodiment, phase detection circuit 1008 is constructed as shown and described above with respect to any of FIGS. 1 through 7. Phase detection circuit 1008 provides output signals to loop filters 1010-1, . . . , 1010-M. Loop filters 1010-1, . . . , 1010-M are coupled to inputs of oscillators 1006-1, . . . , 1006-M, respectively. Control circuit 1012 is coupled to first and second multiplexers 1002 and 1004 and phase detection circuit 1008.

In operation, multiplexed phase lock loop 1000 is operable to lock oscillators 1006-1, . . . , 1006-M in phase and frequency with input signals INPUT 1, . . . , INPUT M, respectively. Control circuit 1012 selects an input signal from first multiplexer 1002 and a corresponding signal from one of oscillators 1006-1, . . . , 1006-M. These selected signals are provided to phase detection circuit 1008 which detects any phase difference between the signals. This phase difference is provided to the selected loop filter 1010-1, . . . , 1010-M to adjust the settings for the oscillator 1006-1, . . . , 1006-M. In this manner, phase detection circuit 1008 can be used to control the number of oscillators 1006-1, . . . , 1006-M. Each of loop filters 1010-1, . . . , 1010-M provides an output signal for phase lock loop 1000.

VII. Additional Embodiments of Output Circuits

Figure 11:
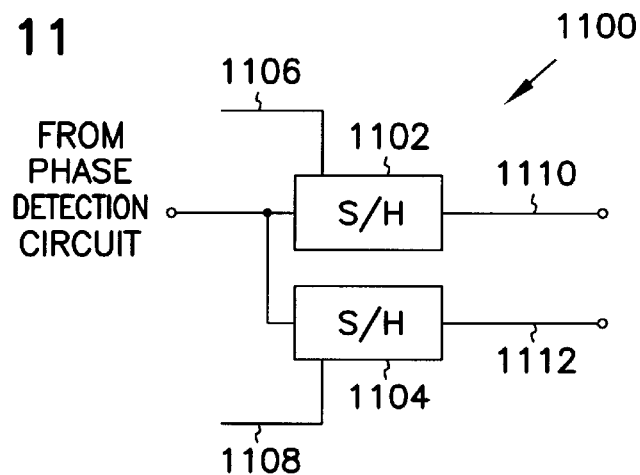
FIGS. 11, 12 and 13 are block diagrams that provide alternative embodiments of output circuits for phase detection circuits according to the teachings of the present invention.
Figure 12:
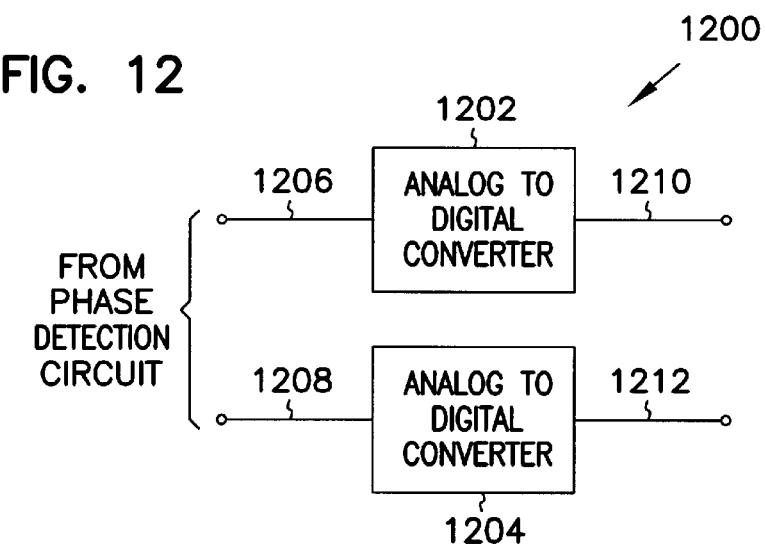
Figure 13:
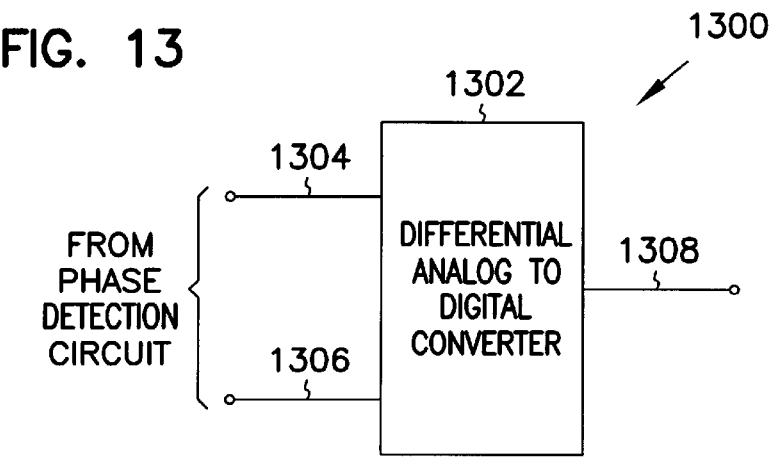

FIGS. 11, 12 and 13 provide alternative embodiments of output circuits used in phase detection circuits 106, 818, and 1008. In these embodiments, the bulk of phase detection circuits 106, 818, and 1008 are constructed as shown and described in the '044 Application with respect to FIGS. 1, 2, 3, 4, 5, 7, or 9. FIGS. 11, 12 and 13 provide additional circuitry coupled to the output of the circuits shown in the '044 Application to allow successive measurements to be taken by the phase detection circuit.

FIG. 11 illustrates an embodiment of an output circuit 1100 including sample and hold circuits (S/H) 1102 and 1104. Both sample and hold circuits 1102 and 1104 are coupled to an output of a phase detection circuit. Each sample and hold circuit 1102 and 1104 is coupled to a control signal 1106 and 1108, respectively.

In operation, output circuits 1100 allows successive measurements to be taken by a phase detection circuits using duty cycle modulation. Initially, a first measurement is produced by the phase detection circuit and provided to the input of both sample and hold circuits 1102 and 1104. Control signal 1106 selects sample and hold circuit 1102 to sample the output from the phase detector and hold that signal at output 1110 of sample and hold circuit 1102. When the second measurement is produced by the phase detection circuit, control signal 1108 causes sample and hold circuit 1104 to sample the output voltage and hold the voltage at output 1112 of sample and hold circuit 1104. Thus multiple measurements may be taken in provided as output signals from a single phase detection circuit.

FIG. 12 illustrates an embodiment of an output circuit indicated generally at 1200 and constructed according to the teachings of the present invention. Output circuit 1200 includes first and second analog to digital converters 1202 and 1204. Inputs 1206 and 1208 of analog to digital converters 1202 and 1204, respectively, are coupled to first and second outputs of the phase detection circuit. Analog to digital converters 1202 and 1204 provide first and second digital outputs 1210 and 1212. These digital outputs provide a differential signal representative of a phase difference. If analog to digital converters 1202 and 1204 operate with sufficient speed, the phase detection circuit may be used to generate successive measurements.

FIG. 13 illustrates an embodiment of an output circuit indicated generally at 1300 and constructed according to the teachings of the present invention. The output circuit 1300 includes differential analog to digital converter 1302. Converter 1302 includes first and second inputs 1304 and 1306 that are coupled to a phase detection circuit. Converter 1302 provides one or more digital output signals at output 1308.

Conclusion

Although specific embodiments have been illustrated and described herein, it will be appreciated by those of ordinary skill in the art that any arrangement which is calculated to achieve the same purpose may be substituted for the specific embodiment shown.

This application is intended to cover any adaptations or variations of the present invention. For example, the input signals can be duty cycle modulated using other techniques. Further, current sources other than a current mirror may be used with the second stage of the phase detector. The differential output from two sampling capacitors can be provided as output with or without a reference voltage off-set. Further, the selection of input signals can be done with a single multiplexer, two multiplexers or other appropriate circuitry for selecting among a plurality of pairs of input signals. A single pair of transducers can also be used in the transit time flow meter. Further, the output of the phase detector circuit can be provided as analog or digital signals by use of appropriate output circuits, e.g., analog to digital converters, sample and hold circuits, or other output processing circuits.

What is claimed is:

1. A transit time flow meter, comprising:

a first pair of transducers;

a second pair of transducers;

wherein the first and second pair of transducers are placeable in relation to a conduit to transmit ultrasonic signals through a fluid;

a multiplexed phase detector, coupled to the first and second pairs of transducers, the multiplexed phase detector using duty cycle modulation to determine a first phase difference between signals received from the first pair of transducers and a second phase difference between signals received from the second pair of transducers; and a data processing circuit, responsive to the multiplexed phase detector, that generates a measure of fluid flow in the conduit based on the first and second phase differences.

2. The flow meter of claim 1, wherein the multiplexed phase detector comprises:

at least one multiplexer having inputs that are coupleable to receive the signals received from the first and second pairs of transducers and having a pair of outputs;

a phase detection circuit, coupled to the pair of outputs of the at least one multiplexer, the phase detection circuit using duty cycle modulation to generate at least one signal that represents the first and second phase differences; and a control circuit, coupled to the at least one multiplexer and the phase detection circuit, the control circuit providing a signal to the at least one multiplexer to select a pair of input signals and providing control signals to the phase detection circuit to control the generation of the at least one signal.

3. The flow meter of claim 2, wherein the at least one multiplexer comprises first and second multiplexers, each having a first input coupled to a first one of the transducers in each pair of transducers and a second input coupled to the other of the transducers in each pair of transducers.

4. The flow meter of claim 2, wherein the phase detection circuit includes:

a duty cycle modulator that modulates the duty cycle of intermediate signals based on a phase difference between signals provided by the at least one multiplexer; and at least two pair of capacitors that are selectively charged based on the intermediate signals such that each pair of capacitors provides, in succession, a signal that is related to the phase difference between signals provided by the at least one multiplexer.

5. The flow meter of claim 4, and further including a pulse selector circuit that selects a number of pulses in the intermediate signals to be used to charge one of the at least two pair of capacitors.

6. The flow meter of claim 4, and further including:

a first differential amplifier coupled to a first pair of capacitors of the at least two pair of capacitors; and a second differential amplifier coupled to the other pair of capacitors of the at least two pair of capacitors.

7. The flow meter of claim 6, and further including a summing amplifier coupled to the output of the first differential amplifier and coupled to the output of the second differential amplifier.

8. The flow meter of claim 7, and further including a divider coupled to the output a summing amplifier.

9. The flow meter of claim 4, and further including at least two amplifiers, each coupled to one pair of the at least two pair of capacitors to provide at least two outputs signals for the multiplexed phase detector.

10. The flow meter of claim 4, and further including an amplifier have a first input coupled to a first one of the capacitors in each of the at least two pair of capacitors and a second input coupled to the second one of the capacitors in each of the at least two pair of capacitors.

11. The flow meter of claim 4, and further including:
a first switch that selectively couples a first one of the capacitors in each of the at least two pair of capacitors together to average the voltage on the capacitors; and
a second switch that selectively couples a second one of the capacitors in each of the at least two pair of capacitors together to average the voltage on the capacitors.

12. The flow meter of claim 4, and further including a switch coupled in parallel with each capacitor in the at least two pair of capacitors that is used to selectively clear the voltage on the capacitor under the control of the control circuit.

13. The flow meter of claim 2, and further including first and second sample and hold circuits coupled to the phase detection circuit to sample and hold its output on successive phase measurements.

14. The flow meter of claim 2, and further including first and second analog to digital converters coupled to the phase detection circuit to digitize first and second outputs of the phase detection circuit.

15. The flow meter of claim 2, and further including a differential analog to digital converter coupled to the phase detection circuit to digitize the outputs of the phase detection circuit.

16. The flow meter of claim 1, wherein the data processing circuit includes a transmitter for transmitting data to a remote processor.

17. The flow meter of claim 1, wherein the first pair of transducers are provided in a first probe and the second pair of transducers are provided in a second probe.

18. The flow meter of claim 17, wherein the first and second probes are independent.

19. The flow meter of claim 17, wherein the first and second probes are in the same housing.

20. A method for detecting flow in a fluid, the method comprising:
transmitting ultrasonic signals between first and second transducers;
receiving time-shifted ultrasonic signals at the first and second transducers;
selecting the time-shifted ultrasonic signals from the first and second transducers;
determining a first phase difference between the selected, time-shifted ultrasonic signals from the first and second transducers using duty cycle modulation;
transmitting ultrasonic signals between third and fourth transducers;
receiving time-shifted ultrasonic signals at the third and fourth transducers;
selecting time-shifted ultrasonic signals from the third and fourth transducers;
determining a second phase difference between the time-shifted ultrasonic signals from the third and fourth transducers using duty cycle modulation; and
generating a flow measurement based on the first and second phase differences.

21. The method of claim 20, wherein determining the first phase difference comprises:
modulating a duty cycle of first and second intermediate signals from a first duty cycle based on a phase difference between the time-shifted ultrasonic signals from the first and second transducers; and
creating a differential signal based on the modulated duty cycles of the first and second intermediate signals that is related to the phase difference between the time-shifted ultrasonic signals from the first and second transducers.

22. The method of claim 21, and further comprising selecting a number of pulses in the first and second intermediate signals.

23. The method of claim 21, wherein modulating the duty cycle comprises modulating the duty cycles of the first and second intermediate signals from nominal, fifty percent duty cycles.

24. The method of claim 21, wherein creating a differential signal comprises creating a differential output signal that is proportional to twice the phase difference between the time-shifted ultrasonic signals from the first and second transducers.

25. The method of claim 21, and further comprising converting the time-shifted ultrasonic signals from the first and second transducers to signals with substantially fifty percent duty cycles prior to modulating the duty cycles of the first and second intermediate signals.

26. The method of claim 21, wherein determining the second phase difference comprises:
modulating a duty cycle of first and second intermediate signals from a first duty cycle based on a phase difference between the time-shifted ultrasonic signals from the third and fourth transducers; and
creating at least one additional differential signal based on the modulated duty cycles of the first and second intermediate signals that is related to the phase difference between the time-shifted ultrasonic signals from the third and fourth transducers.

27. The method of claim 26, and further comprising digitizing the differential signal and the at least one additional differential signal.

28. The method of claim 26, and further comprising sampling and holding the differential signal and then sampling and holding the at least one additional differential signal.

29. The method of claim 21, wherein generating a flow measurement based on the first and second phase differences comprises generating a volumetric flow measurement.

* * * * *